US00PP29581P2

(12) United States Plant Patent
Ault

(10) Patent No.: US PP29,581 P2
(45) Date of Patent: Aug. 7, 2018

(54) ***VERONICA* PLANT NAMED 'BLUE SPRITE'**

(50) Latin Name: ***Veronica* hybrid**
Varietal Denomination: Blue Sprite

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 23 days.

(21) Appl. No.: 15/530,285

(22) Filed: Dec. 19, 2016

(51) Int. Cl.
*A01H 5/02* (2018.01)

(52) U.S. Cl.
USPC ..... Plt./251

(58) Field of Classification Search
USPC ..... Plt./251
See application file for complete search history.

*Primary Examiner* — Keith O Robinson
(74) *Attorney, Agent, or Firm* — Penny J. Aguirre

(57) ABSTRACT

A new cultivar of *Veronica*, 'Blue Sprite', that is characterized by its flowering stems that are compact, its secondary inflorescences that are long in length and produce flowers over a greater length along the raceme than is typical for this type of *Veronica*, its abundance of flowering stems, its high resistance to powdery mildew and rust, and its foliage that is flushed with a red-violet color when exposed to cold temperatures.

2 Drawing Sheets

Botanical classification: *Veronica* hybrid.
Cultivar designation: 'Blue Sprite'.

BACKGROUND OF THE INVENTION

The present invention relates to a new and distinct cultivar of *Veronica*, botanically a *Veronica* of hybrid origin and will be referred to hereafter by its cultivar name, 'Blue Sprite'. 'Blue Sprite' represents a new herbaceous perennial grown for landscape use.

The new invention arose from an ongoing breeding program by the Inventor in Glencoe, Ill. The objectives of the breeding program are to develop improved cultivars of interspecific hybrids of *Veronica* with novel ornamental traits such as disease resistance, drought tolerance, cold hardiness and compact stems.

The new cultivar arose as a seedling derived from open pollination of an unnamed and unpatented plant of *Veronica allionii* in 2007. The male parent is therefore unknown and the new cultivar is presumed to be of interspecific origin based on it characteristics. 'Blue Sprite' was selected in 2009 as a single unique plant amongst the resulting seedlings.

Asexual propagation of the new cultivar was first accomplished by shoot tip cuttings by the Inventor in 2009 in Glencoe, Ill. Asexual propagation by shoot tip cuttings and division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Blue Sprite' as a unique cultivar of *Veronica*.

1. 'Blue Sprite' exhibits flowering stems that are compact.
2. 'Blue Sprite' exhibits secondary inflorescences that are long in length and produce flowers over a greater length along the raceme than is typical for this type of *Veronica*.
3. 'Blue Sprite' exhibits an abundance of flowering stems.
4. 'Blue Sprite' exhibits high resistance to powdery mildew and rust.
5. 'Blue Sprite' exhibits foliage that is flushed with a red-violet color when exposed to cold temperatures.

The female parent of 'Blue Sprite' differs from 'Blue Sprite' in having longer flowering stems with less of the stem covered with flowers, in lacking secondary inflorescences, and in exhibiting some re-bloom in late summer. 'Blue Sprite' can be most closely compared to *Veronica allionii* 'Blue Pixie' (not patented) and *Veronica spicata* 'Blue Nana' (not patented). 'Blue Pixie' and 'Blue Nana' are similar to 'Blue Sprite' in having a blooming period from early June to mid July and in having flowering stems that are comparably shorter in length compared to spicate type *Veronica* varieties. 'Blue Pixie' differs from 'Blue Sprite' in having flowering stems and secondary stems that are shorter in length with less of the stem length bearing flowers, having petioles that are longer in length, and in having foliage that remains green in color when exposed to cold temperatures. 'Blue Nana' differs to 'Blue Sprite' in having a blooming period that starts one week later, in having some re-bloom in late summer, in having less flower coverage of the plant at peak bloom, and in lacking secondary inflorescences.

BRIEF DESCRIPTION OF THE DRAWINGS

The accompanying colored photographs illustrate the overall appearance and distinct characteristics of the new *Veronica*. The photographs were taken of 'Blue Sprite' as grown outdoors in a trial plot in Glencoe, Ill.

The photograph in FIG. 1 provides a view of a 3 year-old plant of 'Blue Sprite' in bloom.

Figure 1:
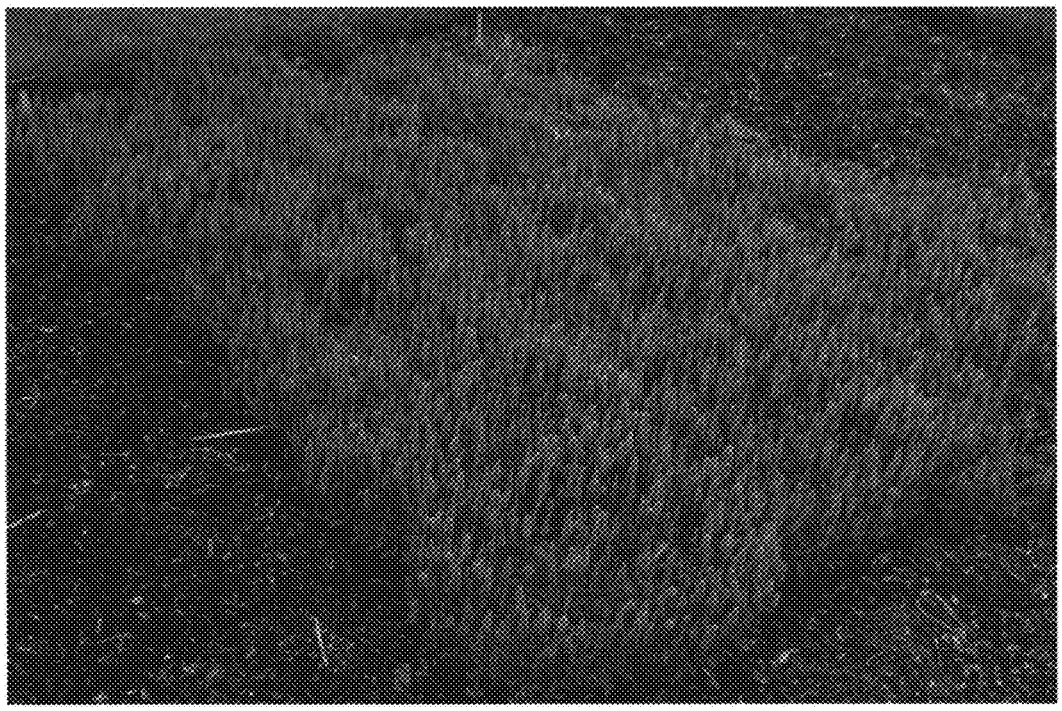
Figure 2:
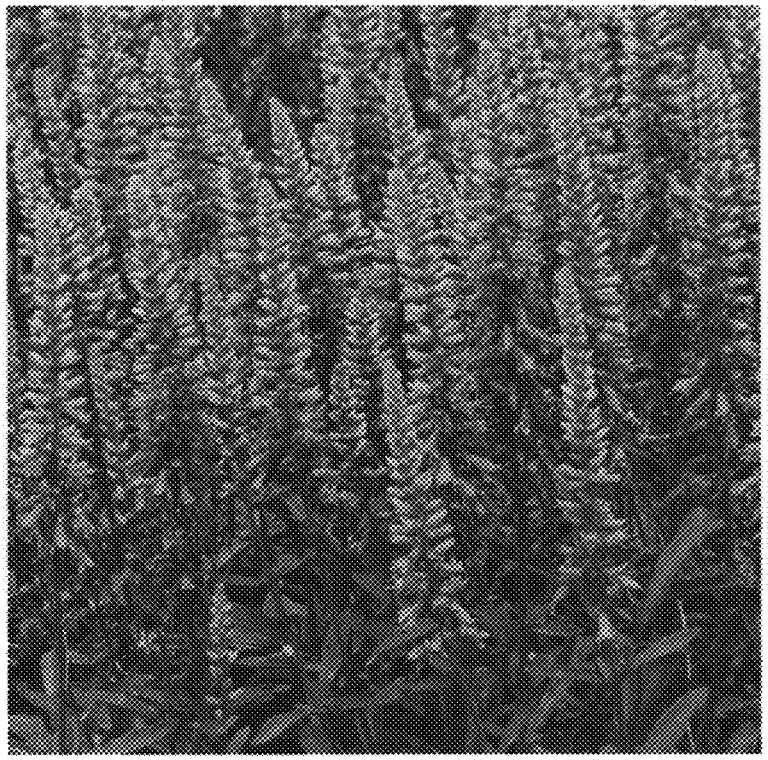

The photograph in FIG. 2 provides a close-up view of the inflorescences of a 5 year-old plant of 'Blue Sprite'.

Figure 3:
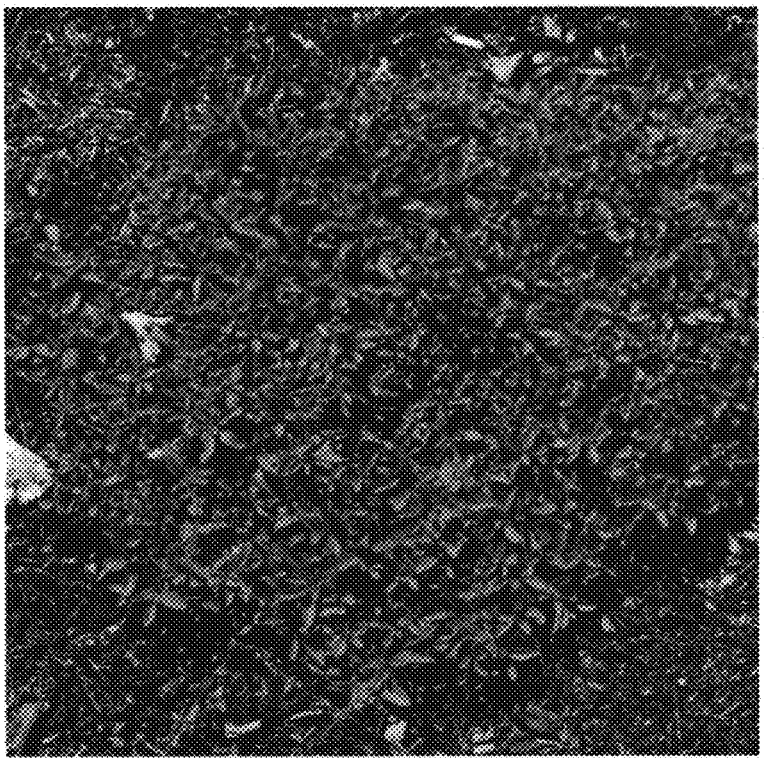

The photograph in FIG. 3 provides a close-up view of the foliage of 'Blue Sprite' 3 years in age.

The colors in the photographs may differ slightly from the color values cited in the detailed botanical description, which accurately describe the colors of the new *Veronica*.

DETAILED BOTANICAL DESCRIPTION

The following is a detailed description of the new cultivar as observed for a plant 4-years-in-age as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Continuously from mid-June to mid-July in Illinois.

*Plant type*.—Herbaceous perennial.

*Plant habit*.—Compact with branched flowering stems, forms a low, dense shrubby habit as a mature plant.

*Height and spread*.—Vegetative growth reaches about 2 cm in height and 25 cm in spread (foliage) as a two year-old plant in the landscape from a rooted cutting (2.5 cm in height and 45 cm in width as a 4 year-old plant).

*Hardiness*.—Hardy to U.S.D.A. Zones 4a to 7a.

*Diseases*.—Highly resistant to rust (*Puccinia veronicae-longifoliae*) and powdery mildew (*Sphaerotheca* spp.).

*Growth rate*.—Good vigor for a compact *Veronica*.

*Propagation*.—Division or shoot tip cuttings.

*Root description*.—Root color; 199A, fibrous.

*Root development*.—Shoot tip cuttings treated with rooting solution and placed under mist will root in about one month in a 72-cell liner and a young plant will fully root in a 3-inch container from a 72-cell liner in about 6 months.

Stem description:

*Shape*.—Round.

*Stem quantity*.—Average of 15 main stems, average of 50 lateral stems per plant.

*Stem color*.—Main, older stems 199A, young and lateral stems; 191A and 197A, become flushed with 187A in cool temperatures.

*Stem size*.—Average of 2 mm in diameter, main stems; an average of 8 cm in length, lateral stems; non-blooming lateral stems an average of 2.5 cm and flowering lateral stems an average of 10 cm (excluding inflorescence).

*Stem surface*.—Main stems; slightly glossy and glabrous, young and lateral stems moderately to densely covered with long puberulent hairs up to 5 mm in length, fine and woolly in texture, 196A in color.

*Stem aspect*.—Main stems grow horizontally to the soil, lateral stems grow upward.

*Branching habit*.—Freely branching from the base.

Foliage description:

*Leaf division*.—Simple.

*Leaf arrangement*.—Opposite.

*Leaf shape*.—Elliptic to linear.

*Leaf size*.—An average of 4 cm in length and 1.5 cm in width.

*Leaf number*.—Average of 14 per main and lateral branch.

*Leaf base*.—Cuneate.

*Leaf apex*.—Acute to bluntly acute.

*Leaf margin*.—Serrate.

*Leaf venation*.—Pinnate, surfaces match leaf surface.

*Leaf surface*.—Upper and lower surfaces are dull, both surfaces sparsely covered with pubescence that match leaf color.

*Leaf color*.—Young upper surface; 147A, young lower surface; 147B, become flushed with 187A in cool temperatures on both surfaces.

*Leaf attachment*.—Petiolate.

*Leaf petiole*.—Average of 5 mm in length, 1 mm in width, matches leaf color, surfaces are glabrous.

Flower description:

*Inflorescence type*.—Compound terminal and secondary racemes of rotate-shaped flowers.

*Lastingness of inflorescence*.—Individual flowers last 3 to 4 days, inflorescence lasts about 10 days, blooms from bottom of raceme towards apex.

*Inflorescence size*.—Average of 8 cm in length and 2 cm in diameter on terminals and 3 cm in length and 2 cm in width on secondary inflorescences.

*Inflorescence quantity*.—45 per plant.

*Flower type*.—Rotate.

*Flower number*.—Average of 200 flowers and buds per inflorescence, 9,000 flowers and buds per plant.

*Flower fragrance*.—Faint.

*Flower buds*.—Narrowly ovate in shape, about 5 mm in length and 2 mm in diameter, young bud color; 157A, mature bud before burst; N82B.

*Flower size*.—About 8 mm in depth and 6 mm in diameter.

*Peduncles*.—Primary peduncle; 9 cm in length and 2 mm in diameter, held vertically, strong, dull surface moderately to densely covered with pubescence, 144A in color, secondary peduncles; an average of 3.5 mm in length and 1 mm in diameter, held at an average angle of 45°, strong, dull surface is moderately covered with pubescence, 144B in color.

*Pedicels*.—Not present, peduncles only.

*Calyx*.—Rotate in shape, attached to peduncle, average of 2 mm in length and 2 mm in diameter.

*Sepals*.—5, rotate, ovate to narrowly ovate in shape, base is cuneate with lower 2% fused, matte and glabrous inner and outer surfaces moderately covered with pubescence, entire margin, acute apex, 2 mm in length, 1 mm in width, inner and outer surfaces NN137A and 138A in color.

*Petals*.—4, obovate to ovate in shape, obtuse to acute apex, lower 20% fused, entire margin, color of upper and lower surfaces when opening; 85B with hues of 92C, base is 85D, color of upper and lower surfaces when fully open; N89A with hues of 94D, base is 85B, up to 5 mm in length and 3 mm in width, matte and glabrous on both surfaces.

Reproductive organs:

*Gynoecium.*—1 Pistil, style; and average of 7 mm in length and 94A in color, glabrous surface, stigma; minute, round in shape, 90A in color, glabrous surface, ovary is superior, 1 mm in diameter, 145A in color, glabrous surface.

*Androecium.*—2 stamens, filament; average of 5 mm in length, a blend of 92A and NN155C in color, glabrous surface, anthers; are dorsifixed and elliptic in shape, average of 1 mm in length and 0.5 mm in width, varying between 165B and a blend of 79A and 81A in color, glabrous surface, pollen is moderate in quantity and 4A in color.

*Fruit.*—Fruit and seed production has not been observed.

It is claimed:

1. A new and distinct cultivar of *Veronica* plant named 'Blue Sprite' as herein illustrated and described.

* * * * *